(12) United States Patent
Tomita (10) Patent No.: US 10,351,872 B2
(45) Date of Patent: Jul. 16, 2019

(54) GENE FOR SHORTENING CULM OF GRAMINEOUS PLANT AND METHOD FOR PRODUCING SHORT-CULMED GRAMINEOUS PLANT

(71) Applicants: NATIONAL UNIVERSITY CORPORATION TOTTORI UNIVERSITY, Tottori (JP); NATIONAL UNIVERSITY CORPORATION SHIZUOKA UNIVERSITY, Shizuoka (JP)

(72) Inventor: Motonori Tomita, Shizuoka (JP)

(73) Assignee: NATIONAL UNIVERSITY CORPORATION SHIZUOKA UNIVERSITY, Shizuoka (JP)

( * ) Notice: Subject to any disclaimer, the term of this patent is extended or adjusted under 35 U.S.C. 154(b) by 1002 days.

(21) Appl. No.: 14/388,918

(22) PCT Filed: Mar. 7, 2013

(86) PCT No.: PCT/JP2013/056339
§ 371 (c)(1),
(2) Date: Sep. 29, 2014

(87) PCT Pub. No.: WO2013/146171
PCT Pub. Date: Oct. 3, 2013

(65) Prior Publication Data
US 2015/0113684 A1 Apr. 23, 2015

(30) Foreign Application Priority Data

Mar. 29, 2012 (JP) ................. 2012-077453

(51) Int. Cl.
*C12N 15/29* (2006.01)
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8218* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 6,307,126 B1 | 10/2001 | Harberd et al. | |
| 2004/0123343 A1* | 6/2004 | La Rosa | C07K 14/415 800/278 |
| 2004/0250315 A1 | 12/2004 | Okawa et al. | |
| 2006/0123507 A1 | 6/2006 | Ashikari et al. | |

FOREIGN PATENT DOCUMENTS

| | | |
|---|---|---|
| JP | 2000-505290 | 5/2000 |
| JP | 2003-260 | 1/2003 |
| JP | 2007-49994 | 3/2007 |
| JP | 2008-237138 | 10/2008 |
| WO | 03/008540 | 1/2003 |

OTHER PUBLICATIONS

GenBank Accession No. AP005398 (Submitted Jul. 12, 2004).*
A Dictionary of Biology (6 ed.) Oxford University Press, online 2014 (retrieved May 14, 2017).*
UniProt Accession No. Q6ES26 (Submitted Aug. 16, 2004).*
Xu et al. The Plant Journal 9.6 (1996): 879-889.*
Uozu et al. Plant Physiology 122.3 (2000): 853-860.*
International Search Report dated Apr. 9, 2013 in International (PCT) Application No. PCT/JP2013/056339.
International Preliminary Report on Patentability and Written opinion dated Oct. 1, 2014 in International (PCT) Application No. PCT/JP2013/056339.
Yu et al., "Hypothetical protein OsJ_06252 [Oryza sativa Japonica Group]", GenBank Accession No. EAZ22584.1, Feb. 2009.
Tanisaka et al., "Two Useful Semidwarfing Genes in a Short-culm Mutant line HS90 of Rice (*Oryza sativa L.*)", Breeding Science, vol. 44, 1994, pp. 397-403.
Itoh et al., "Modification of Rice Plant Height by Suppressing the Height-Controlling Gene, *D18*, in Rice", Breeding Science, vol. 52, 2002, pp. 215-218.
Tomita et al., "Identification and genetic diagnosis of rice novel QTL associating with both semidwarfism and late-maturity", Breeding research, 2011, vol. 13, No. 2, p. 18.
Tomita, "The gametic lethal gene *gal*: activated only in the presence of the semidwarfing gene *d60* in rice", Rice Genetics III, Ed. G. S. Khush, International Rice Research Institute, pp. 396-403, 1996.
Tomita et al., "Developmental cytology on gametic abortion caused by induced complementary genes *gal* and *d60* in j aponica rice", Advances in Rice Genetics, Ed. Khush, International Rice Research Institute, pp. 178-181, 2003.
Office Action dated Nov. 17, 2015 in corresponding Chinese Application No. 201380028681.1, with English translation.
Sasaki et al., Oryza sativa nipponbare (GA3) genomic DNA, chromosome 2, PAC clone: P0669G10, Oryza sativa Japonica group, 2002, 3 pages, cited in CA.

(Continued)

*Primary Examiner* — Mykola V. Kovalenko
*Assistant Examiner* — Charles Logsdon
(74) *Attorney, Agent, or Firm* — Wenderoth, Lind & Ponack, L.L.P.

(57) ABSTRACT

The purpose of the invention is to identify a short-culm gene other than the sd1 gene and produce a short-culmed gramineous plant by utilizing a short-culm gene other than the sd1 gene. The present invention provides a method for producing a short-culmed gramineous plant utilizing gene d60 for shortening the culm of a gramineous plant, wherein the method for producing a short-culmed gramineous plant is characterized in that the expression of Os02g0280200 is suppressed. The present invention also provides a short-culmed gramineous plant and the like in which the expression of Os02g0280200 is suppressed.

5 Claims, 3 Drawing Sheets

Specification includes a Sequence Listing.

(56) References Cited

OTHER PUBLICATIONS

Japanese Office Action dated Feb. 23, 2016 in corresponding Japanese Patent Application No. 2012-077453 (English translation).
Minihikari, registered variety database, Jul. 11, 2008, URL, http://www.hinsyu.maff.go.jp/vips/CMM/apCMM112.aspx?TOUROKU_NO=19985&LANGUAGE=Japanese (English translation).
Second Office Action dated Jun. 22, 2016 in corresponding Chinese Application No. 201380028681.6, with English Translation.
Tanaka et al., NM_001053089.1, GenBank, pp. 1-5, 20100608, Jun. 8, 2010.

* cited by examiner

Control

Transformant with cDNA
full length antisense gene

Transformant with second
exon antisense gene

SEQUENCE LISTING

```
<160> NUMBER OF SEQ ID NOS: 16

<210> SEQ ID NO 1
<211> LENGTH: 1510
<212> TYPE: DNA
<213> ORGANISM: Olyza sativa L.

<400> SEQUENCE: 1
atggcggcga agctgcaggg aggaggagga ggagcggcgg tgatggcggt ggtggtggtg      60
gcgatggtcg ccggcgcggc gtccggcggc aacttctacg aggagtgcga cgcgacgtgg     120
gagccgcaga actgctggtc gtcggacaac ggcaagagcc tgtcgctggc gctggtcagc     180
aactcctccg gctccatgat ccgctccaag cggcagttcg tctacggctc cgtctccacc     240
tccgtccagc tcgtccccgg caactccgcc ggcaccgtca ccaccttcta cgtacgccat     300
tgatcacccc catcgatcga tcgattatat atatatctca tcttcgatct gcatccattt     360
ccttccgccg atcgatcgat cgattgattg attggtacac gattttgtgc gtgcgtgtgt     420
gatggatcga tgcagacgtc gtcgctgggt gacaagcacg acgagatcga cttcgagttc     480
ctgggcaacg agaccggaca accctacacc atccacacca acgtctacgc caacggcgtc     540
ggcgacaagg agatgcagtt caagccgtgg ttcgacccca ccgacggctc ccacaactac     600
```

```
accatctcct ggaccccctg caggatcgtg taagcgcaca cacacacgct cacctacatt      660
caggcagagg cggagccagg tgtggggcag cttgggccca ggccccacac ctggcagaaa      720
aaataccaag gaatttacta attttttttat taaaattcgt ttaagaagtt catactctag    780
tgattaagcc ccactcttga cataatcctg gctccgcccc tgcattcagg ttttgcaatt     840
tcgctttcgg caaaaatttc ggtcatttca atagaaccga aatttccata ttttttgacc    900
aaaattttct gaaatttttaa cacaatttaa ctgaatttaa ctaaatttcg tctaaattca   960
aaaaaaaatg aaaaaaaccg aaagtttcag tcgagatatt gacttgccaa aggggggggt    1020
ccgaaattac cgaaatttca atcactgcct atattgtgaa actggtcggt acaagcaact    1080
taataacggt aacaattaat gcaggtggta catcgatggg atgcccatca gggtgttccg    1140
caactaccag agcagcaacg gcgtggcgtt cccgacgtgg cagccgatgt acgcctactc    1200
gagcatatgg gcggcggagg actgggccac gcagaagggg agggtcaaga cggactggag    1260
caaggcgccg ttcgtcgcca actaccacgg catcgacctc gacgtctgcg agtgctacgg    1320
cggcgactgc gtgtacggct gcgccgccgc gttcaaccag gcggcggct gcgccggcca     1380 gcagctcacc ggcgacgaga tggggcagat gaagtgggtg caggacaact tcaggatcta    1440
cgactactgc gtcgactaca gcggttcaa cggccagatg gcgccggagt gcagcctgcc    1500
acaatactga                                                            1510
```

<210> SEQ ID NO 2
<211> LENGTH: 1510
<212> TYPE: DNA
<213> ORGANISM: Olyza sativa L.

<400> SEQUENCE: 2

```
atggcggcga agctgcaggg aggaggagga ggagcggcgg tgatggcggt ggtggtggtg      60
gcgatggtcg ccggcgcggc gtccggcggc aacttctacg aggagtgcga cgcgacgtgg     120
gagccgcaga actgctggtc gtcggacaac ggcaagagcc tgtcgctggc gctggtcagc    180
aactcctccg gctccatgat ccgctccaag cggcagttcg tctacggctc cgtctccacc   240
tccgtccagc tcgtccccgg caactccgcc ggcaccgtca ccaccttcta cgtacgccat    300
tgatcacccc catcgatcga tcgattatat atatatctca tcttcgatct gcatccattt   360
ccttccgccg atcgatcgat cgattgattg attggtacac gattttgtgc gtgcgtgtgt   420
gatggatcga tgcagacgtc gtcgctgggt gacaagcacg acgagatcga cttcgagtcc   480
ctgggcaacg agaccggaca accctacacc atccacacca acgtctacgc caacggcgtc    540
ggcgacaagg agatgcagtt caagccgtgg ttcgacccca ccgacggctc ccacaactac    600
accatctcct ggaccccctg caggatcgtg taagcgcaca cacacacgct cacctacatt      660
caggcagagg cggagccagg tgtggggcag cttgggccca ggccccacac ctggcagaaa      720
aaataccaag gaattaacta attttttttat taaaattcgt ttaagaagtt catactctag    780
tgattaagcc ccactcttga cataatcctg gctccgcccc tgcattcagg ttttgcaatt     840
tcgctttcgg caaaaatttc ggtcatttca atagaaccga aatttccata ttttttgacc    900
aaaattttct gaaatttttaa cacaatttaa ctgaatttaa ctaaatttcg tctaaattca   960
aaaaaaaatg aaaaaaaccg aaagtttcag tcgagatatt gacttgccaa aggggggggt    1020
ccgaaattac cgaaatttca atcactgcct atattgtgaa actggtcggt acaagcaact    1080
taataacggt aacaattaat gcaggtggta catcgatggg atgcccatca gggtgttccg    1140
caactaccag agcagcaacg gcgtggcgtt cccgacgtgg cagccgatgt acgcctactc    1200
```

```
gagcatatgg cgccggagg actgggccac gcagaagggg agggtcaaga cggactggag    1260
caaggcgccg ttcgtcgcca actaccacgg catcgacctc gacgtctgcg agtgctacgg    1320
cggcgactgc gtgtacggct gcgccgccgc gttcaaccag gcggcggct gcgccggcca    1380 gcagctcacc ggcgacgaga tgggggcagat gaagtgggtg caggacaact tcaggatcta    1440
cgactactgc gtcgactaca agcggttcaa cggccagatg gcgccggagt gcagcctgcc    1500
acaatactga                                                          1510
```

<210> SEQ ID NO 3
<211> LENGTH: 296
<212> TYPE: PRT
<213> ORGANISM: Olyza sativa L.

<400> SEQUENCE: 3

```
Met Ala Ala Lys Leu Gln Gly Gly Gly Gly Ala Ala Val Met Ala
1               5                   10                  15

Val Val Val Ala Met Val Ala Gly Ala Ser Gly Gly Asn Phe
            20                  25                  30

Tyr Glu Glu Cys Asp Ala Thr Trp Glu Pro Gln Asn Cys Trp Ser Ser
        35                  40                  45

Asp Asn Gly Lys Ser Leu Ser Leu Ala Leu Val Ser Asn Ser Ser Gly
    50                  55                  60

Ser Met Ile Arg Ser Lys Arg Gln Phe Val Tyr Gly Ser Val Ser Thr
65                  70                  75                  80

Ser Val Gln Leu Val Pro Gly Asn Ser Ala Gly Thr Val Thr Thr Phe
                85                  90                  95

Tyr Thr Ser Ser Leu Gly Asp Lys His Asp Glu Ile Asp Phe Glu Phe
            100                 105                 110

Leu Gly Asn Glu Thr Gly Gln Pro Tyr Thr Ile His Thr Asn Val Tyr
        115                 120                 125

Ala Asn Gly Val Gly Asp Lys Glu Met Gln Phe Lys Pro Trp Phe Asp
    130                 135                 140

Pro Thr Asp Gly Ser His Asn Tyr Thr Ile Ser Trp Thr Pro Cys Arg
145                 150                 155                 160

Ile Val Trp Tyr Ile Asp Gly Met Pro Ile Arg Val Phe Arg Asn Tyr
                165                 170                 175

Gln Ser Ser Asn Gly Val Ala Phe Pro Thr Trp Gln Pro Met Tyr Ala
            180                 185                 190

Tyr Ser Ser Ile Trp Ala Ala Glu Asp Trp Ala Thr Gln Lys Gly Arg
        195                 200                 205

Val Lys Thr Asp Trp Ser Lys Ala Pro Phe Val Ala Asn Tyr His Gly
    210                 215                 220

Ile Asp Leu Asp Val Cys Glu Cys Tyr Gly Gly Asp Cys Val Tyr Gly
225                 230                 235                 240

Cys Ala Ala Ala Phe Asn Gln Gly Gly Gly Cys Ala Gly Gln Gln Leu
                245                 250                 255

Thr Gly Asp Glu Met Gly Gln Met Lys Trp Val Gln Asp Asn Phe Arg
            260                 265                 270

Ile Tyr Asp Tyr Cys Val Asp Tyr Lys Arg Phe Asn Gly Gln Met Ala
        275                 280                 285

Pro Glu Cys Ser Leu Pro Gln Tyr
    290                 295
```

```
<210> SEQ ID NO 4
<211> LENGTH: 296
<212> TYPE: PRT
<213> ORGANISM: Olyza sativa L.

<400> SEQUENCE: 4

Met Ala Ala Lys Leu Gln Gly Gly Gly Gly Ala Ala Val Met Ala
1               5                   10                  15

Val Val Val Val Ala Met Val Ala Gly Ala Ala Ser Gly Gly Asn Phe
            20                  25                  30

Tyr Glu Glu Cys Asp Ala Thr Trp Glu Pro Gln Asn Cys Trp Ser Ser
        35                  40                  45

Asp Asn Gly Lys Ser Leu Ser Leu Ala Leu Val Ser Asn Ser Ser Gly
    50                  55                  60

Ser Met Ile Arg Ser Lys Arg Gln Phe Val Tyr Gly Ser Val Ser Thr
65                  70                  75                  80

Ser Val Gln Leu Val Pro Gly Asn Ser Ala Gly Thr Val Thr Thr Phe
                85                  90                  95

Tyr Thr Ser Ser Leu Gly Asp Lys His Asp Glu Ile Asp Phe Glu Ser
            100                 105                 110

Leu Gly Asn Glu Thr Gly Gln Pro Tyr Thr Ile His Thr Asn Val Tyr
        115                 120                 125

Ala Asn Gly Val Gly Asp Lys Glu Met Gln Phe Lys Pro Trp Phe Asp
    130                 135                 140

Pro Thr Asp Gly Ser His Asn Tyr Thr Ile Ser Trp Thr Pro Cys Arg
145                 150                 155                 160

Ile Val Trp Tyr Ile Asp Gly Met Pro Ile Arg Val Phe Arg Asn Tyr
                165                 170                 175

Gln Ser Ser Asn Gly Val Ala Phe Pro Thr Trp Gln Pro Met Tyr Ala
            180                 185                 190

Tyr Ser Ser Ile Trp Ala Ala Glu Asp Trp Ala Thr Gln Lys Gly Arg
        195                 200                 205

Val Lys Thr Asp Trp Ser Lys Ala Pro Phe Val Ala Asn Tyr His Gly
    210                 215                 220

Ile Asp Leu Asp Val Cys Glu Cys Tyr Gly Gly Asp Cys Val Tyr Gly
225                 230                 235                 240

Cys Ala Ala Ala Phe Asn Gln Gly Gly Gly Cys Ala Gly Gln Gln Leu
                245                 250                 255

Thr Gly Asp Glu Met Gly Gln Met Lys Trp Val Gln Asp Asn Phe Arg
            260                 265                 270

Ile Tyr Asp Tyr Cys Val Asp Tyr Lys Arg Phe Asn Gly Gln Met Ala
        275                 280                 285

Pro Glu Cys Ser Leu Pro Gln Tyr
    290                 295

<210> SEQ ID NO 5
<211> LENGTH: 194
<212> TYPE: DNA
<213> ORGANISM: Olyza sativa L.

<400> SEQUENCE: 5
acgtcgtcgc tgggtgacaa gcacgacgag atcgacttcg agttcctggg caacgagacc    60
ggacaaccct acaccatcca caccaacgtc tacgccaacg gcgtcggcga caaggagatg   120
cagttcaagc cgtggttcga ccccaccgac ggctccccaca actacaccat ctcctggacc   180
ccctgcagga tcgt                                                     194
```

<210> SEQ ID NO 6
<211> LENGTH: 194
<212> TYPE: DNA
<213> ORGANISM: Olyza sativa L.

<400> SEQUENCE: 6

```
acgtcgtcgc tgggtgacaa gcacgacgag atcgacttcg agtccctggg caacgagacc      60
ggacaaccct acaccatcca caccaacgtc tacgccaacg gcgtcggcga caaggagatg     120
cagttcaagc cgtggttcga ccccaccgac ggctcccaca actacaccat ctcctggacc     180
ccctgcagga tcgt                                                      194
```

<210> SEQ ID NO 7
<211> LENGTH: 65
<212> TYPE: PRT
<213> ORGANISM: Olyza sativa L.

<400> SEQUENCE: 7

```
Thr Ser Ser Leu Gly Asp Lys His Asp Glu Ile Asp Phe Glu Phe Leu
1               5                   10                  15

Gly Asn Glu Thr Gly Gln Pro Tyr Thr Ile His Thr Asn Val Tyr Ala
            20                  25                  30

Asn Gly Val Gly Asp Lys Glu Met Gln Phe Lys Pro Trp Phe Asp Pro
        35                  40                  45

Thr Asp Gly Ser His Asn Tyr Thr Ile Ser Trp Thr Pro Cys Arg Ile
    50                  55                  60

Val
65
```

<210> SEQ ID NO 8
<211> LENGTH: 65
<212> TYPE: PRT
<213> ORGANISM: Olyza sativa L.

<400> SEQUENCE: 8

```
Thr Ser Ser Leu Gly Asp Lys His Asp Glu Ile Asp Phe Glu Ser Leu
1               5                   10                  15

Gly Asn Glu Thr Gly Gln Pro Tyr Thr Ile His Thr Asn Val Tyr Ala
            20                  25                  30

Asn Gly Val Gly Asp Lys Glu Met Gln Phe Lys Pro Trp Phe Asp Pro
        35                  40                  45

Thr Asp Gly Ser His Asn Tyr Thr Ile Ser Trp Thr Pro Cys Arg Ile
    50                  55                  60

Val
65
```

<210> SEQ ID NO 9
<211> LENGTH: 891
<212> TYPE: DNA
<213> ORGANISM: Artificial Sequence
<220> FEATURE:
<223> OTHER INFORMATION: Antisence sequence

<400> SEQUENCE: 9

```
tcagtattgt ggcaggctgc actccggcgc catctggccg ttgaaccgct tgtagtcgac      60
gcagtagtcg tagatcctga agttgtcctg cacccacttc atctgcccca tctcgtcgcc     120
ggtgagctgc tggccggcgc agccgccgcc ctggttgaac gcggcggcgc agccgtacac     180
```

```
gcagtcgccg ccgtagcact cgcagacgtc gaggtcgatg ccgtggtagt tggcgacgaa    240
cggcgccttg ctccagtccg tcttgaccct ccccttctgc gtggcccagt cctccgccgc    300
ccatatgctc gagtaggcgt acatcggctg ccacgtcggg aacgccacgc cgttgctgct    360
ctggtagttg cggaacaccc tgatgggcat cccatcgatg taccacacga tcctgcaggg    420
ggtccaggag atggtgtagt tgtgggagcc gtcggtgggg tcgaaccacg gcttgaactg    480
catctccttg tcgccgacgc cgttggcgta gacgttggtg tggatggtgt agggttgtcc    540
ggtctcgttg cccaggaact cgaagtcgat ctcgtcgtgc ttgtcaccca gcgacgacgt    600
gtagaaggtg gtgacggtgc cggcggagtt gccggggacg agctggacgg aggtggagac    660
ggagccgtag acgaactgcc gcttggagcg gatcatggag ccggaggagt tgctgaccag    720
cgccagcgac aggctcttgc cgttgtccga cgaccagcag ttctgcggct cccacgtcgc    780
gtcgcactcc tcgtagaagt tgccgccgga cgccgcgccg gcgaccatcg ccaccaccac    840
caccgccatc accgccgctc ctcctcctcc tccctgcagc ttcgccgcca t             891
```

```
<210> SEQ ID NO 10
<211> LENGTH: 194
<212> TYPE: DNA
<213> ORGANISM: Artificial Sequence
<220> FEATURE:
<223> OTHER INFORMATION: Antisence sequence

<400> SEQUENCE: 10
acgatcctgc aggggtcca ggagatggtg tagttgtggg agccgtcggt ggggtcgaac     60
cacggcttga actgcatctc cttgtcgccg acgccgttgg cgtagacgtt ggtgtggatg   120
gtgtagggtt gtccggtctc gttgcccagg aactcgaagt cgatctcgtc gtgcttgtca   180
cccagcgacg acgt                                                     194
```

```
<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tcgatcgatt gattgattgg t                                              21
```

```
<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ccatggcatg cacatataca tgc                                            23
```

```
<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
ttttgtaggt agaagtctag atcag                                          25
```

```
<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
ggaaattcga gctcggtacc atggc                                              25

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
tgtaggtaga agtctagaac gatcc                                              25

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
aattcgagct cggtaccacg tcgtc                                              25
```

GENE FOR SHORTENING CULM OF GRAMINEOUS PLANT AND METHOD FOR PRODUCING SHORT-CULMED GRAMINEOUS PLANT

TECHNICAL FIELD

The present invention relates to a gene for shortening the height of a gramineous plant, a method of producing a short-culmed gramineous plant, and a short-culmed gramineous plant.

BACKGROUND ART

Gramineous plants are agriculturally very important plants, including rice, wheat, barley, oat, rye, proso millet, foxtail millet, Japanese millet, corn, finger millet, sorghum, and the like. Gramineous plants having long culms tend to be lodged by strong wind such as typhoon, and thereby the crop yields are serious decreased.

In development of varieties having loading resistance, by seeking a short culm gene, breeding of gramineous plants having short culms has been carried out for many years. However, when the height of a plant is shortened, the panicles and grains of the plant often become reduced in size. Such a short culm gene is not desired from the viewpoint of productivity. Therefore, there is a need for a short culm gene that does not affect panicles and grains, but suitably shortens only plant height.

Among the short culm genes that have ever been found, only sd1 has been put to practical use. The sd1 gene results in a character called "semidwarf", in which the length of panicles is normal and the height of a whole plant is short. The sd1 gene is a defective form of a C20-oxidase gene for gibberellin (GA) biosynthesis. Varieties of short-culmed rice that are currently cultivated in many areas of the world include Calrose 76 developed in U.S.A., IR 36 developed in south-eastern Asia, Hikari-Shinseiki developed in Japan, and the like. Genetic analyses of these short culm varieties showed that all of the varieties have the same locus as that of the semidwarfing gene sd1. In other words, cultivation of the current short-culmed gramineous plants is governed by only one specific gene, and the only one specific gene is widely used. Considering the purpose of breeding to maintain and expand the genetic diversity of varieties, use of short culm genes other than gene sd1 in breeding to develop varieties having lodging resistance should be encouraged, and new short culm genes are needed.

Recently, a semidwarfing gene, d60 has been newly found (Non-patent literatures 1 and 2). The d60 gene is a gene for shortening the height of a plant by about 20 cm as compared with the height of a plant that does not have the d60 gene.

Coexistence of the semidwarfing gene d60 with gal, which is a gametic lethal gene and universally present in rice, is fatal to both male and female gametes. Therefore, $F_1$ cross (D60d60Galgal) between Koshihikari d60 line, or a variety or line having d60 such as Hokuriku 100 (genotype: d60d60GalGal) and another variety or line (D60D60galgal) shows pollen and seed fertility of 75%, and $F_2$ progeny shows a specific hereditary mode in which it segregates at the ratio of six fertile long-culmed plants (4 D60D60:2 D60d60GalGal):two partial sterile long-culmed plants (D60d60Galgal=F1 type):one short-culmed plant (d60d60GalGal). Thus, Gal is essential to the heredity of d60. The d60 gene is a valuable short culm gene, which would not be obtained in nature without simultaneous artificial mutation of Gal.

The semidwarfing gene d60 has been found to be located on the second chromosome of rice plants and shown to be a gene independent genetically and functionally from sd1 which is located on the first chromosome (Patent Literature 1). A method of selecting gramineous plants having gene d60 and gene Gal has also been developed, in which the method comprises that the presence of gene d60 on the second chromosome and/or the presence of gene Gal on the fifth chromosome which is essential to the heredity of gene d60 are determined using DNA markers or gene markers (Patent Literature 1).

However, the d60 gene has never been identified and the shortening function of d60 has never been elucidated. The d60 gene has never been put to practical use.

CITATION LIST

Patent Literature

Patent Literature 1: JP-A 2008-237138

Non-Patent Literature

Non-Patent Literature 1: Tomita, M., The gametic lethal gene gal, activated only in the presence of the semidwarfing gene d60 in rice. In Rice Genetics III (Ed. G. S. Khush, ISBN 971-22-0087-6), International Rice Research Institute, pp. 396-403 (1996)

Non-Patent Literature 2: Tomita, M., Yamagata, H. and Tanisaka, T., Developmental cytology on gametic abortion caused by induced complementary genes gal and d60 in j aponica rice. In Advances in Rice Genetics (Eds. G. S. Khush, D. S. Brar and B. Hardy, ISBN 971-22-0199-6), International Rice Research Institute, pp. 178-181 (2003)

SUMMARY OF INVENTION

Problem to be Solved by the Invention

Objectives of the present invention are to identify of a short culm gene other than sd1 and to create a short-culmed gramineous plant using the short culm gene other than sd1.

Solution to Problems

Under the above-described circumstances, the present inventor focused use of gene d60 and intensively studied to identify the gene and elucidate its culm-shortening function. As a result of fine mapping of gene d60, the present inventor found that a region of a d60 candidate gene was located about 10.2 to 10.5 Mb from the short arm end of the second chromosome. Then, the present inventor performed sequencing of the d60 candidate gene and finally identified gene d60 as a functionally-defective form of an Os02g0280200 gene. Thus, the present invention was completed.

Specifically, the present invention provides:

[1] A method of producing a short-culmed gramineous plant, which comprises suppressing the expression of Os02g0280200 gene in a gramineous plant,

[2] The method according to [1], wherein the expression of the Os02g0280200 gene is suppressed by an antisense method or a mutagenesis method,

[3] The method according to [2], wherein the gramineous plant is transformed with a vector containing an antisense sequence of the full length cDNA of the Os02g0280200 gene,

[4] The method according to [2], wherein the gramineous plant is transformed with a vector containing an antisense sequence of the second exon of the Os02g0280200 gene,

[5] The method according to [2], wherein a mutation from thymine to cytosine is introduced at position 479 in a nucleotide sequence of the Os02g0280200 gene,

[6] The method according to [5], wherein the gramineous plant is transformed with a vector containing a nucleotide sequence shown in SEQ ID NO:2,

[7] The method according to [5], wherein the gramineous plant is transformed with a vector containing a nucleotide sequence encoding a protein comprising an amino acid sequence shown in SEQ ID NO:4,

[8] The method according to [5], wherein the gramineous plant is transformed with a vector containing a nucleotide sequence shown in SEQ ID NO:6,

[9] The method according to [5], wherein the gramineous plant is transformed with a vector containing a nucleotide sequence encoding a protein comprising an amino acid sequence shown in SEQ ID NO:8,

[10] A short-culmed gramineous plant wherein the expression of an Os02g0280200 gene is suppressed,

[11] A short culm gene comprising a nucleotide sequence shown in SEQ ID NO:2,

[12] A short culm gene encoding a protein comprising an amino acid sequence shown in SEQ ID NO:4,

[13] A DNA consisting of an antisense sequence of the full length cDNA of an Os02g0280200 gene,

[14] A DNA consisting of an antisense sequence of the second exon of an Os02g0280200 gene,

[15] A DNA consisting of an antisense sequence of a nucleotide sequence encoding a protein comprising an amino acid sequence shown in SEQ ID NO:3, and

[16] A DNA consisting of an antisense sequence of a nucleotide sequence encoding a protein comprising an amino acid sequence shown in SEQ ID NO:7.

Effects of the Invention

According to the present invention, a gramineous plant only whose height is suitably shortened and whose panicles and grains are not affected can be obtained by suppressing the expression of an Os02g0280200 gene in a gramineous plant, without depending on the conventional gene sd1. Therefore, according to the present invention, a useful gramineous plant satisfying both lodging resistance and productivity can be obtained.

MODE FOR CARRYING OUT THE INVENTION

In the present invention, gene d60 was identified as follows. Line (D60D60galgal) in which the second chromosome of Koshihiraki was partially substituted by that of indica variety Kasalath was crossed with Koshihikari d60 line (d60d60GalGal), and then, progeny $F_2$ was obtained. From the $F_2$, short-culmed homozygous (d60d60GalGal) plants were selected, and subjected to fine mapping by using SSR (Simple Sequence Repeat) markers on the second chromosome which showed differences between japonica varieties and indica varieties. Linkage between each of the SSR markers and gene d60 was investigated by DNA polymorphism and then, a location showing a recombination value of 0% was determined. A recombination value is calculated by the following equation:

Recombination value=(Number of recombinant gametes/Total number of gametes)×100, wherein complete linkage shows a recombination value of 0%.

The present inventor's previous study found that gene d60 was present on a locus 2.8 cM from SSR marker RM452 (Patent Literature 1). Therefore, in the present invention, fine mapping was performed using RM452 and various SSR markers located near RM452. As a result, the recombination value between RM12970 and gene d60 was 0%. Therefore, it was found that a candidate region of gene d60 was located about 10.2 to 10.5 Mb from the short arm end of the second chromosome of rice.

Among putative genes located about 10.2 to 10.5 Mb from the short arm end of the second chromosome of rice, Os02g0280200 and Os02g0280300 were subjected to sequencing analyses between Koshihikari and Koshihikari d60 line. As a result, a nucleotide mutation from thymine (T) to cytosine (C) was found at position 479 in a nucleotide sequence of the second exon of the Os02g0280200 gene. In addition, as a result of amino acid sequence analyses between Koshihikari and Kosihikari d60 line, an amino acid mutation form phenylalanine (F) to serine (S) was found at the position corresponding to the above-described mutation in the nucleotide sequence.

An antisense sequence of the full length cDNA of the Os02g0280200 gene or an antisense sequence of the second exon of the Os02g0280200 gene was introduced into Koshihikari to obtain a short-culmed plant. Thus, gene d60 was identified as a functionally-defective form of the Os02g0280200 gene.

An example of the full length nucleotide sequence of the Os02g0280200 gene of Koshihirari is shown in SEQ ID NO:1. An example of the full length nucleotide sequence of the Os02g0280200 gene of Koshihirari d60 line is shown in SEQ ID NO:2. A nucleotide sequence of the second exon of the Os02g0280200 gene of Koshihirari is shown in SEQ ID NO:5. A nucleotide sequence of the second exon of the Os02g0280200 gene of Koshihirari d60 line is shown in SEQ ID NO:6. An example of an amino acid sequence encoded by the full length nucleotide sequence of the Os02g0280200 gene of Koshihirari is shown in SEQ ID NO:3. An example of an amino acid sequence encoded by the full length nucleotide sequence of the Os02g0280200 gene of Koshihirari d60 line is shown in SEQ ID NO:4. An amino acid sequence encoded by the second exon of the Os02g0280200 gene of Koshihirari is shown in SEQ ID NO:7. An amino acid sequence encoded by the second exon of the Os02g0280200 gene of Koshihirari d60 line is shown in SEQ ID NO:8.

Therefore, the first aspect of the present invention provides a method of producing a short-culmed gramineous plant which comprises suppressing the expression of an Os02g0280200 gene. Os02g0280200 indicates a locus on the second chromosome of rice and disclosed in the Rice Annotation Project Database (RAP-DB) and the like. As used herein, a gene present on Os02g0280200 is referred to as an "Os02g0280200 gene". The present inventor identified gene d60 as a functionally-defective form of the Os02g0280200 gene, and then found that the culm of a gramineous plant can be shortened by suppressing the expression of the gene. Therefore, the Os02g0280200 gene has a similar sequence to that of xyloglucan transglycosylase (XTH) gene, and 360 probably catalyzes cross-linkage between molecules of xyloglucan in a cell wall to participate morphogenesis. Probably, d60 lacks the catalytic function as described above and thereby produces a short culm.

In the present invention, the "Os02g0280200 gene" includes the Os02g0280200 gene of rice and the corresponding genes of the other gramineous plants. For example, the Os02g0280200 gene includes a gene located 10388558 to 10390067 nucleotides from the short arm end of the second chromosome of rice disclosed in the Rice Annotation Project Database (RAP-DB) Build4, and the corresponding genes of the other gramineous plants. The Os02g0280200 gene of rice has a mRNA sequence disclosed in NCBI Reference Sequence Accession NO. NM_001053089. An amino acid sequence of a protein encoded by the Os02g0280200 gene of rice is disclosed in NCBI Reference Sequence Accession NO. NP_001046554. The genes of gramineous plants other than rice which correspond to the Os02g0280200 gene can be identified by a conventional method, for example, homology search using a database containing genome information of a plant of interest and information of a nucleotide sequence of the Os02g0280200 gene of rice or an amino acid sequence encoded by the nucleotide sequence.

In the present invention, the "short-culmed gramineous plant" means a gramineous plant of which the height is shortened. The short-culmed gramineous plant is preferably a gramineous plant in which the length of panicles and the size of grains are normal and the height of the whole plant is only shortened. In the present invention, the "short culm gene" means a gene for shortening the culm of a gramineous plant. The short culm gene is preferably a gene resulting in the above-described "short-culmed gramineous plant".

In the present invention, the "gramineous plant" includes rice, wheat, barley, oat, rye, prose millet, foxtail millet, Japanese millet, corn, finger millet, sorghum, and the like. Preferably, rice can be used. Various varieties and lines belonging to *Oryza sativa L*. can be used as rice. For example, japonica varieties such as Koshihikari, Nipponbare, Hitomebore, Hinohikari, Akitakomachi, Kinuhikari, Nanatsuboshi, Haenuki, Kirara397, Tsugaru Roman, Masshigura, etc. and indica varieties such as Kasalath, etc. can be used.

In the present invention, the "suppression" of the expression of the Os02g0280200 gene means that the gene is not expressed, or the expression amount of the gene is decreased as compared with a control in which the expression of the gene is not suppressed.

In the present invention, the suppression of the expression of the Os02g0280200 gene may be performed by any method conventionally used in the art. A method of suppressing the expression of the Os02g0280200 gene is not particularly limited, and for example, includes an antisense method, a mutagenesis method, and an RNA interference method. In the case of an antisense method, for example, an antisense sequence of the full length cDNA of the Os02g0280200 gene or an antisense sequence of the second exon of the Os02g0280200 gene is introduced into a gramineous plant. In the case of a mutagenesis method, a mutation that suppresses the expression of the Os02g0280200 gene is introduced into its nucleotide sequence. For example, although not limited thereto, a mutation of T (thymine) to C (cytosine) may be introduced at position 44 of the second exon of the Os02g0280200 gene, for example at position 479 of the full length nucleotide sequence of the Os02g0280200 gene. For example, a nucleotide sequence shown in SEQ ID NO:2 or SEQ ID NO:6 or a nucleotide sequence encoding an amino acid sequence shown in SEQ ID NO:4 or SEQ ID NO:8 can be introduced into a gramineous plant.

In the present invention, introduction of a desired gene sequence into a gramineous plant may be performed by any method conventionally used in the art. Examples of such a conventional gene introduction method include, but not limited to, an *agrobacterium*-mediated transformation method, a particle gun-mediated transformation method, an electroporation method, and a polyethyleneglycol (PEG)-mediated transformation method.

In the present invention, transformation of a gramineous plant can be performed using various nucleic acid molecules designed to suppress the expression of the Os02g0280200 gene or to alter the structure of the Os02g0280200 gene. Example of such nucleic acid molecules include an antisense sequence of the full length cDNA of the Os02g0280200 gene, for example the sequence shown in SEQ ID NO:9; an antisense sequence of the second exon of the Os02g0280200 gene, for example the sequence shown in SEQ ID NO:10; a nucleotide sequence of the Os02g0280200 gene containing mutation T→C at position 479, for example the sequence shown in SEQ ID NO:2 or SEQ ID NO:6; and a nucleotide sequence encoding the amino acid sequence shown in SEQ ID NO:4 or SEQ ID NO:8.

For the transformation, a cell, for example protoplast, callus or embryo, a piece of tissue, or a plant body of a gramineous plant can be preferably used.

In the method of the present invention, a gramineous plant can be transformed, for example, by using a vector containing a desired nucleic acid molecule. The vector may contain a variety of promoter sequences capable of expressing the desired gene. Examples of the promoter include, but limited to, rice Actin 1 promoter, and 35S promoter. The vector can contain a variety of selectable markers that allow selection of transformed cells into which the vector has been integrated. Examples of the selectable marker include, but limited to, an antibiotic resistance gene and a herbicide resistance gene, for example, a neomycin resistance gene, a kanamycin resistance gene, a hygromycin resistance gene, a bialaphos resistance gene, and a streptomycin resistance gene. The vector can also contain a terminator. Such a terminator is particularly not limited as long as it functions within a plant body. Examples of the terminator include a cauliflower mosaic virus terminator, and a terminator derived from a nopaline synthetase gene terminator (Nos terminator).

For example, when a gramineous plant is transformed by using the *agrobacterium* method in the method of the present invention, various plasmid vectors including commercially available plasmid vectors, for example pSTARA R-5, pRI201-ON, etc. can be used.

After transformation, cells are grown in a selection medium for a certain period, and then, transformed plant cells are selected. From the transformed cells thus obtained, a whole plant body can be regenerated to obtain a short-culmed gramineous plant.

Thus, the second aspect of the present invention provides a short-culmed gramineous plant in which the expression of the Os02g0280200 gene is suppressed. The present invention preferably provides a short-culmed gramineous plant in which the length of panicles and the size of grains are normal and the height of the whole plant is only shortened.

The third aspect of the present invention provides a short culm gene that is a functionally-defective form of the Os02g0280200 gene. The present invention preferably provides a short culm gene comprising a nucleotide sequence shown in SEQ ID NO:2 or SEQ ID NO:6, or a short culm gene encoding a protein comprising an amino acid sequence shown in SEQ ID NO:4 or SEQ ID NO:8. The present invention more preferably provides a short culm gene consisting of a nucleotide sequence shown in SEQ ID NO:2 or a short culm gene encoding a protein consisting of an amino acid sequence shown in SEQ ID NO:4.

The present invention further provides a DNA consisting of an antisense sequence of the full length cDNA of the Os02g0280200 gene, or a DNA consisting of an antisense sequence of the second exon of the Os02g0280200 gene, preferably a DNA consisting of a nucleotide sequence shown in SEQ ID NO:9, or a DNA consisting of a nucleotide sequence shown in SEQ ID NO:10, for use in production of a short-culmed gramineous plant. The present invention also provides a DNA consisting of an antisense sequence of a nucleotide sequence encoding a protein consisting of an amino acid sequence shown in SEQ ID NO:3, or an antisense sequence of a nucleotide sequence encoding a protein consisting of an amino acid sequence shown in SEQ ID NO:7, for use in production of a short-culmed gramineous plant.

The present invention is further explained in detail by reference to the following Examples, to which the present invention is not limited.

EXAMPLE 1

Fine Mapping of Gene d60

Line (D60D60galgal) in which the second chromosome of Koshihiraki was partially substituted by that of indica variety Kasalath was crossed with Koshihikari d60 line (d60d60GalGal) to obtain $F_1$ (D60d60Galgal). The $F_1$ was self-fertilized to obtain $F_2$. Specifically, line SL204 (D60D60galgal, in which a part of the second chromosome extending from the short arm end to 60.3 cM was substituted by a part of Kasalath) in which the second chromosome of Koshihikari on which d60 was located was partially substituted by that of indica variety Kasalath was crossed with Koshihikari d60 line (d60d60GalGal). Then, 5122 seeds of progeny $F_2$ were sown. At the third-leaf stage, 532 d60-homozygous short-calmed plants (d60d60GalGal) which have short and round leaves were selected and then cultivated in the Field Science Center of the Tottori University. From all of the short-culmed homozygous $F_2$ plants, the leaves were taken as a sample. A DNA was extracted from the leaves.

The extraction of a genomic DNA from each $F_2$ plant was performed as follows. Leaves were taken from the plant, and then kept frozen at −80° C. The leaves were frozen in liquid nitrogen and then ground. To the leaf powder thus obtained, a DNA extraction solution (2% CTAB, 100 mM Tris-HCl, 20 mM EDTA.2Na, 1.4 M NaCl, pH 8.0) was added in an amount equal to the amount of the powder, and then incubated at 55° C. for 90 minutes with shaking. Then, the solution thus obtained was extracted with chloroform/isoamyl alcohol (24:1). A 1/10 volume of 3 M sodium acetate pH 5.2 and then the equal amount of 99.5% isopropanol at −20° C. were added to a supernatant. A polymerized and precipitated DNA was spooled out. The spooled-out DNA was dissolved in 1.5 ml of High-Salt TE (1 M NaCl, 10 mM Tris.HCl, 1 mM EDTA.2Na, pH8.0), subjected to ethanol precipitation, and then dissolved in 500 µl of TE (10 mM Tris-HCl, 1 mM EDTA.2Na, pH8.0). To the solution, a 1/100 volume of an RNase solution (1 mg/ml) was added, and then incubated overnight at 37° C. The mixture was subjected to phenol/chloroform extraction, chloroform extraction, and then ethanol precipitation. Then, the precipitate was dissolved in 500 µl of TS (10 mM Tris-HCl, 1 mM EDTA.2Na, pH8.0).

Then, 48 SSR markers on the short arm of second chromosome which exhibited polymorphism between Kasalath and Koshihikari were used to determine a recombination value between d60 or Gal and the SSR markers, thereby candidates for a locus on which gene d60 was located were narrowed down.

Specifically, 200 ng of the genomic DNA extracted from each $F_2$ plant as desried above as a template, each 200 nM of a forward primer and a reverse primer for each SSR marker, 400 µM dNTPs, 2.5 mM $MgCl_2$, 1×LA PCR BufferII (TAKARA), and 0.5 U LA Taq DNA polymerase (TAKARA) were used to prepare total 25 µl of a reaction solution. PCR was performed 35 cycles using a thermal cycler, in which each cycle consisted of denaturation at 94° C. for 1 minute, annealing at 55° C. for 1 minute, and extension at 72° C. for 1 minute. After PCR, electrophoresis was performed using electrophoresis apparatus QIAxel. As an electrophoresis cartridge, QIAxel DNA screening Kit (2400) was used. A sample was injected at 5 kV for 10 seconds, and electrophoresis was performed at 5 kV for 420 seconds.

Figure 1:
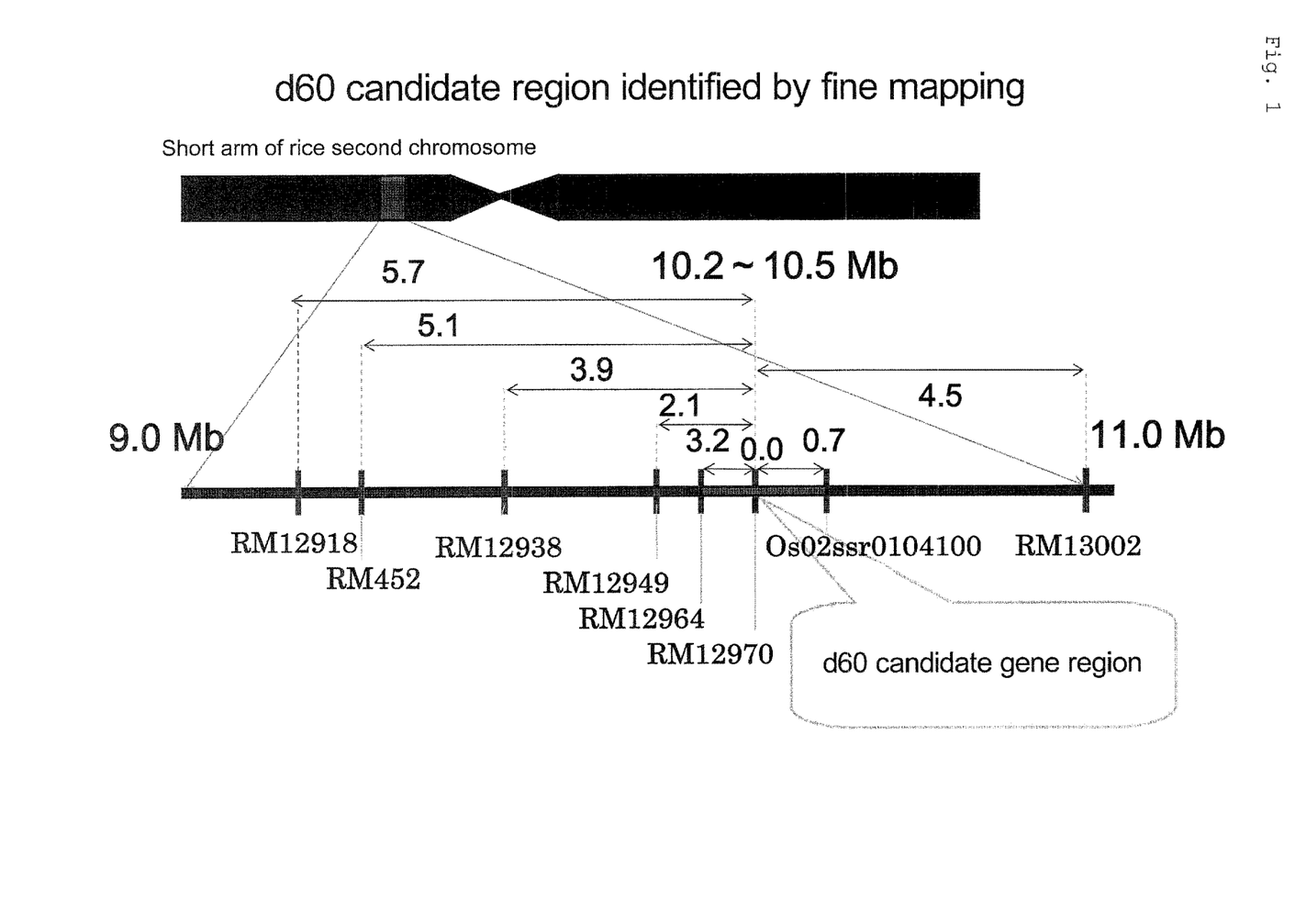
FIG. 1 shows a result of fine mapping of gene d60.

Linkage between gene d60 and each SSR marker was investigated by DNA polymorphism on an electrophoresis result to determine a recombination value between each SSR marker and gene d60. As a result, it was found that of 48 SSR markers, 8 markers located within a region from 9.2 to 11.0 Mb from the short arm end of the second chromosome, i.e., RM12918, RM452, RM12938, RM12949, RM12964, RM12970, Os02ssr0104100 and RM13002 had strong linkage with gene d60. The recombination values between these markers and gene 60 were 5.7 for RM12918 located 9.5 Mb, 5.1 for RM452 located 9.6 Mb, 3.9 for RM12938 located 9.9 Mb, 2.1 for RM12949 located 10.1 Mb, 3.2 for RM12964 located 10.2 Mb, 0.0 for RM 12970 located 10.2 Mb, 0.7 for Os02ssr0104100 located 10.5 Mb, and 4.5 for RM13002 located 10.9 Mb. Based on these recombination values, it was found that d60 is located within a region from 10.2 to 10.5 Mb from the short arm end of the second chromosome (FIG. 1).

EXAMPLE 2

Sequence Analysis of Gene d60

Putative genes Os02g0280200 and Os02g0280300 located about 10.2 to 10.5 Mb from the short arm end of the second chromosome of rice were subjected to sequence analyses as d60 candidate genes.

The Os02g0280200 gene and the Os02g0280300 gene of Koshihikari and Koshihikari d60 line were amplified by PCR, ligated to pUC vector pUC119, cloned by transformation of HST08 derived from Escherichia coli (E. coli) K12 strain with the vector, and then sequenced by a conventional method. Specifically, each 200 ng of the genomic DNAs of Koshihikari and Koshihikari d60 line as a template, each 200 nM of a forward primer (SEQ ID NO:11: TCGATCGATTGATTGATTGGT) and a reverse primer (SEQ ID NO:12: CCATGGCATGCACATATACATGC), 400 µM dNTPs, 2.5 mM $MgCl_2$, 1×LA PCR BufferII (TAKARA), and 0.5 U LA Taq DNA polymerase (TAKARA) were used to prepare total 25 µl of a reaction solution. PCR was performed 35 cycles using a thermal cycler, in which each cycle consisted of denaturation at 94° C. for 1 minute, annealing at 58° C. for 1 minute, and extension at 72° C. for 2 minutes. In addition, denaturation at 94° C. for 5 minutes was performed at the beginning of PCR and synthesis at 72° C. for 5 minutes was performed at the end of PCR. A PCR product was subjected to electrophoresis on 1% agarose gel at 100 V for 35 minutes. For purification of DNA, SUPREC$^R$-PCR (TAKARA) was used. First, 400 µl of sterile water was added to a sample reservoir. The sample reservoir was capped and then centrifuged at 3,500 rpm for 15 minutes. Then, the sample reservoir was removed from a filter vial and placed in a new vial. Next, 20 µl of TE was added to the sample reservoir. After gentle pipetting, the sample reservoir was set upside down and centrifuged at 3,500 rpm for 2 minutes. One µl of the purified PCR product was put in a new micro tube, mixed with 1 µl of pMD 20-T vector (TAKARA) and 3 µl of sterile water, and ligated for 30 minutes. E. coli HST08 Premium Competent cells (TAKARA) were melted in ice just before use, and then gently mixed and homogenized. After 100 µl of the competent cells were transferred into a 14 ml round bottom. tube, a ligation solution was put into the tube. The tube was left in ice for 30 minutes and then incubated at 42° C. for 45 seconds. Then, the tube was left in ice for 1 to 2 minutes, and an SOC medium which was previously kept at 37° C. was added to the tube, followed by shaking at 37° C. for 1 hour. The cells (50 to 100 µl) were spread to a solid LB medium and then left at 37° C. overnight. Form the medium, white colonies were selected and transferred into 3 ml of a liquid LB medium, followed by shaking at 37° C. for 16 hours. From the culture medium (3 ml) of E. coli retaining the recombinant plasmid, a plasmid DNA was purified by an alkaline method. The plasmid thus obtained was used as a template for sequencing by a dideoxy method.

As a result, it was found that in the Os02g0280200 gene region, there was T (thymine)→C (cytosine) mutation at position 479 between the nucleotide sequences of Koshihikari and Kosihikari d60 line. The position 479 in the nucleotide sequence of the Os02g0280200 gene is in the second exon. It was also found that there was F (phenylalanine)→S (serine) mutation at position 112 in the amino acid sequence.

On the other hand, with regard to the Os02g0280300 gene region, no mutation was found between the sequences of Koshihikari and Kosihikari d60 line.

Therefore, it was inferred that gene d60 was a functionally-defective form of the Os02g0280200 gene. An example of the full length nucleotide sequence of the Os02g0280200 gene of Koshihikari is shown in SEQ ID NO:1. An example of the full length nucleotide sequence of the Os02g0280200 gene of Koshihikari d60 line is shown in SEQ ID NO:2. An example of the amino acid sequence encoded by the Os02g0280200 gene of Koshihikari is shown in SEQ ID NO:3. An example of the amino acid sequence encoded by the Os02g0280200 gene of Koshihikari d60 line is shown in SEQ ID NO:4.

EXAMPLE 3

Production of Short-Culmed Rice Using Gene d60

An antisense sequence of the full length cDNA of the Os02g0280200 gene or an antisense sequence of the second exon of the Os02g0280200 gene was introduced into Koshihikari. Introduction of the antisense sequence was performed as described below. Finally, a redifferentiated plant was obtained.

1. Introduction of Binary Vector into *Agrobacterium*

After pSTARA binary vector R-5 containing a rice Actin 1 promoter, a Nos terminator, and rice-derived W548L/ S627I two point mutated acetolactate synthase gene as a selectable marker (product name: pSTARA R-5, manufactured by KUMIAI CHEMICAL INDUSTRIES CO., LTD.) was digested with restriction enzymes XbaI and KpnI, the full length cDNA antisense sequence (SEQ ID NO:9) or the second exon antisense sequence (SEQ ID NO:10) was inserted into the vector. The vector was introduced into *agrobacterium* (*Agrobacterium tumefacience*) EHA105 by electroporation. Transformants were selected on an LB medium containing 100 ppm of spectinomycin.

2. Callus Induction from Scutellum

Sterilized Koshihikari seeds (25 to 35 seeds) were placed on an N6D medium with the embryos up, and then cultivated under light condition (light period: 16 hours) at 30° C. for 5 days.

3. Preculture of *Agrobacterium*

The *agrobacterium* EHA105 into which the binary vector was introduced (from glycerol stock) was cultured in an LB liquid medium (containing spectinomycin at 100 ppm) the day before infection.

4. Co-Culture with *Agrobacterium* Infection

1) Shoot and endosperm parts were removed from the scutellum-derived calluses cultivated for 5 days. The calluses were temporally placed on an N6D medium.

2) Into a 50 ml falcon tube, 40 ml of an AAM solution and then 16 µl of 100 mg/ml acetosyringone were added.

3) The *agrobacteria* that were cultured as described in the above section 3 were collected, suspended and diluted in the AAM solution.

4) The calluses obtained in 1) were put in a new 50 ml falcon tube. The *agrobacterium* suspension obtained in 3) was added to the calluses, and mixed by slow overturning for 1.5 minutes.

5) The mixture obtained in 4) was poured onto a sterilized tea strainer. The tea strainer holding the calluses was placed on sterilized Kimtowel (paper towel) to remove excess fluid.

6) The calluses were placed on a 2N6-AS medium (about 25 calluses per plate) while the calluses were kept from being contact with each other.

7) The calluses were co-cultured under dark condition at 24° C. for 3 days.

5. Removal and Selection of *Agrobacterium*

1) The co-cultured calluses were transferred to a 50 ml falcon tube and then washed with sterile water containing carbenicillin (500 mg/L) 7 to 8 times.

2) After washing, when the washed liquid became transparent, the calluses were left in the sterile water for 10 minutes.

3) Using a new pipette, the calluses were washed until 500 ml of the sterile water was used up, and then transferred onto sterilized Kimtowel (registered trademark) to remove excess water.

4) The calluses were placed on a selection medium (N6D medium) containing 400 mg/L carbenicillin and an appropriate amount of a selection reagent (14 calluses per plate).

5) The calluses were cultured under light condition (light period: 16 hours; the same applies hereafter) at 30° C. for 1 month. (During the second week, the calluses were subcultured.)

6. Redifferentiation to Plant Body

1) When new calluses were grown, they were transferred to redifferentiation medium (RE-III) containing carbenicillin (200 mg/L) and 0.25 µM bispyribac-sodium.

2) The calluses were under light condition at 30° C. for 1 month. (During the second week, the calluses were subcultured.)

3) The calluses were transferred to a hormone-free (HF) medium after shoots and roots were redifferentiated from the calluses.

Figure 2:
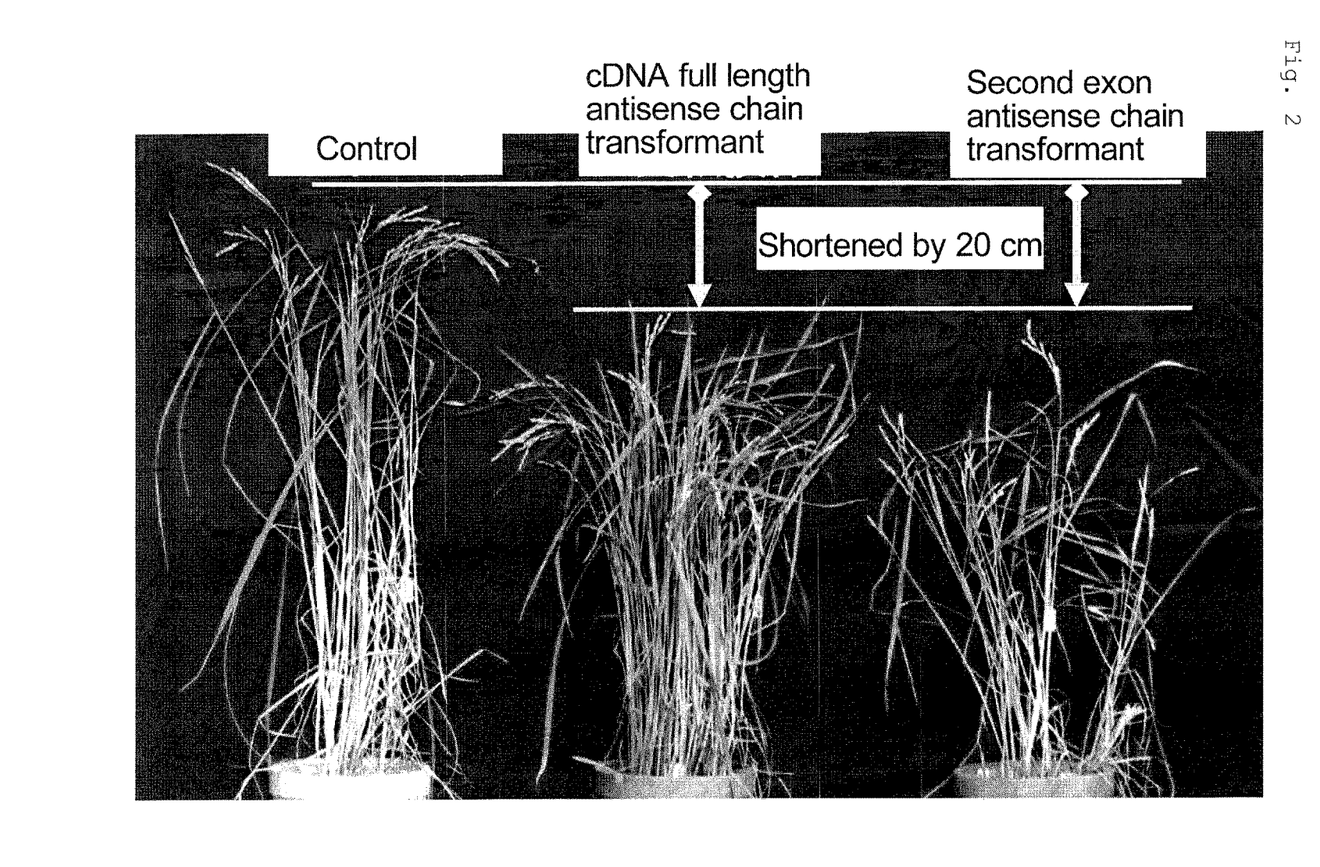
FIG. 2 shows rice plants transformed with antisense sequences of an Os02g0280200 gene.
Figure 3:
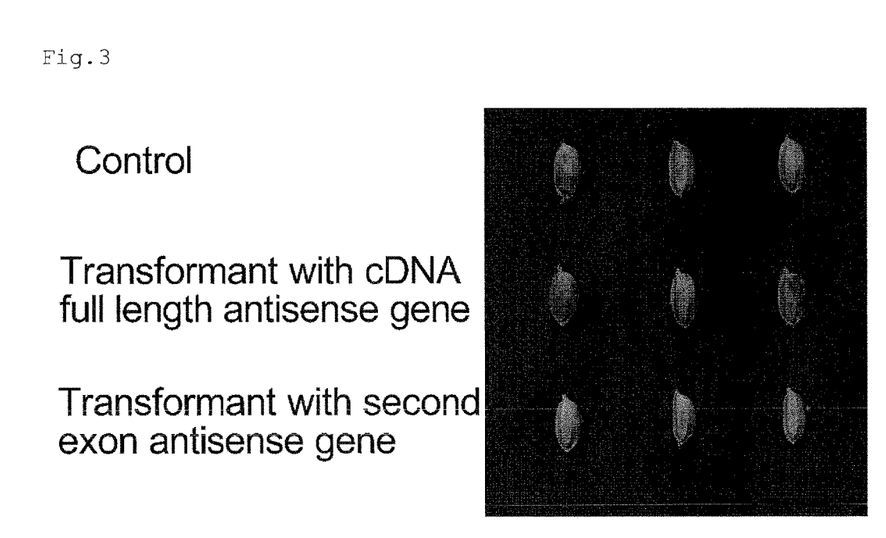
FIG. 3 shows grains of rice plants transformed with antisense sequences of an Os02g0280200 gene.

Results are shown in FIG. 2. As seen from FIG. 2, both a transformant with the full length cDNA antisense sequence of the Os02g0280200 gene and a transformant with the second exon antisense sequence of the Os02g0280200 gene had a height shortened by about 20 cm than that of a control. As the length of a panicle was measured, the control had 14.13 cm panicles, the full length cDNA antisense gene transformant had 14.10 cm panicles, and the second exon antisense gene transformant had 13.40 cm panicles. Both of the transformants had panicle length equal to that of the control. In addition, both of the transformants had grain size equal to that of the control (FIG. 3).

Based on the above results, functional complementation of gene d60 was demonstrated. It was confirmed that gene d60 was a functionally-defective form of the Os02g0280200 gene. In addition, it was demonstrated that a short-culmed gramineous plant was obtained by suppressing the expression of the Os02g0280200 gene.

EXAMPLE 4

Confirmation of Integrated Sequence in Transformant

From each of the transformants obtained in Example 3, a genomic DNA was extracted as described in Example 1. The genomic DNA was subjected to PCR amplification using primers described below, and subjected to electrophoresis, and an amplified band was detected. As a control, non-transformed Koshihikari was used.
Primers for the full length cDNA antisense gene transformant: 3303F and 3303R

```
Forward primer sequence:
                                   (SEQ ID NO: 13)
TTTTGTAGGTAGAAGTCTAGATCAG Reverse primer sequence:
                                   (SEQ ID NO: 14)
GGAAATTCGAGCTCGGTACCATGGC
```

Primers for the second exon antisense gene transformant: 3309F and 3309R

```
Forward primer sequence:
                                   (SEQ ID NO: 15)
TGTAGGTAGAAGTCTAGAACGATCC Reverse primer sequence:
                                   (SEQ ID NO: 16)
AATTCGAGCTCGGTACCACGTCGTC
```

As a result, in the transformant with the full length cDNA antisense gene, a band of 891 bp was detected. In the transformant with the second exon antisense gene, a band of 194 bp was detected. In contrast, for the control, these bands were not detected. Based on these results, it was confirmed that the desired DNA was surely integrated into the transformants obtained in Example 3. Therefore, it was demonstrated that the shortening of rice transformants observed in Example 3 was caused by suppression of the expression of the Os02g0280200 gene.

INDUSTRIAL APPLICABILITY

According to the present invention, a short-culmed gramineous plant can be produced by suppressing the expression of the Os02g0280200 gene of a gramineous plant, without depending on the conventional gene sd1. Since the short-culmed gramineous plant of the present invention has normal size of panicles and grains and only has a shortened height, the short-culmed gramineous plant not only has lodging resistance but also maintains productivity. Therefore, the present invention can be used for production of rice in the field of agriculture, and breeding and genetic improvement of various gramineous plants.

The invention claimed is:

1. A method of producing a short-culmed gramineous plant, which comprises:
   providing a gramineous plant comprising SEQ ID NO: 1 in its genome, and
   introducing a mutation into the nucleic acid sequence of SEQ ID NO:1 in the plant's genome, wherein the mutation is a substitution of thymine to cytosine at position 479 in the nucleotide sequence to suppress the activity of the gene,
   wherein the culm of the short-culmed gramineous plant produced by the method is shortened relative to a control plant grown under the same conditions.

2. A short culm gene comprising the nucleotide sequence of SEQ ID NO:2, wherein the short culm gene is a gene for shortening the culm of a gramineous plant relative to a control plant grown under the same conditions.

3. A short culm gene encoding a protein comprising the amino acid sequence of SEQ ID NO:4, wherein the short culm gene is a gene for shortening the culm of a gramineous plant relative to a control plant grown under the same conditions.

4. A short-culmed gramineous plant comprising in its genome a mutated nucleic acid sequence, wherein the mutated nucleic acid sequence is the sequence of SEQ ID NO:1 that comprises a substitution of thymine to cytosine at position 479 of SEQ ID NO:1, wherein the short-culmed gramineous plant is shortened relative to a plant that does not comprise the mutated nucleic acid sequence and is grown under the same conditions.

5. A method of producing a short-culmed gramineous plant, comprising introducing a polynucleotide comprising the nucleic acid sequence of SEQ ID NO: 2 or a nucleic acid sequence encoding a polypeptide comprising the amino acid sequence of SEQ ID NO: 4, into a gramineous plant not comprising said nucleic acid sequence, by crossing, wherein expression of the nucleic acid in the gramineous plant shortens the culm of the gramineous plant relative to a control plant grown under the same conditions.

* * * * *

UNITED STATES PATENT AND TRADEMARK OFFICE
CERTIFICATE OF CORRECTION

PATENT NO. : 10,351,872 B2
APPLICATION NO. : 14/388918
DATED : July 16, 2019
INVENTOR(S) : Motonori Tomita Page 1 of 1

It is certified that error appears in the above-identified patent and that said Letters Patent is hereby corrected as shown below:

On the Title Page

Item (71) Applicant: change "NATIONAL UNIVERSITY CORPORATION TOTTORI UNIVERSITY, Tottori (JP); NATIONAL UNIVERSITY CORPORATION SHIZUOKA UNIVERSITY, Shizuoka (JP)" to -- NATIONAL UNIVERSITY CORPORATION SHIZUOKA UNIVERSITY, Shizuoka (JP) --.

Signed and Sealed this
Eighth Day of October, 2019

Andrei Iancu
*Director of the United States Patent and Trademark Office*